United States Patent [19]

Cohen et al.

[11] 4,104,397
[45] Aug. 1, 1978

[54] SPIRO (1,3-DIOXOLANE-4,3') QUINUCLIDINE COMPOUNDS

[75] Inventors: Sasson Cohen, Tel-Aviv; Abraham Fisher, Holon, both of Israel

[73] Assignee: The Purdue Frederick Company, Norwalk, Conn.

[21] Appl. No.: 656,056

[22] Filed: Feb. 6, 1976

[30] Foreign Application Priority Data

Nov. 11, 1975 [IL] Israel .......................................... 48452

[51] Int. Cl.² .................. A61K 31/445; C07D 455/02
[52] U.S. Cl. ................................ 424/267; 260/293.53; 424/256
[58] Field of Search .................... 260/293.53; 424/267, 424/256

[56] References Cited

U.S. PATENT DOCUMENTS 3,681,363 8/1972 Elkin et al. ...................... 260/293.53

Primary Examiner—Natalie Trousof
Attorney, Agent, or Firm—Steinberg & Blake

[57] ABSTRACT

Novel spiro (1,3-dioxolane-4,3') quinuclidine compounds of the formula

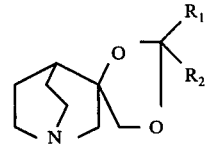

wherein $R_1$ and $R_2$, which may be identical or different, each designates a member of the group hydrogen, alkyl or aryl; a process for the production of these and pharmaceutical compositions of matter containing such compound as active ingredient.

8 Claims, No Drawings

SPIRO (1,3-DIOXOLANE-4,3') QUINUCLIDINE COMPOUNDS

SUMMARY OF THE INVENTION

The present invention relates to novel spiro(1,3-dioxolane-4,3')quincolidine compounds of the general formula

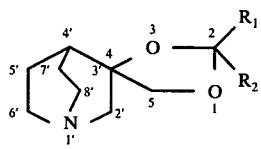

wherein $R_1$ and $R_2$, which may be identical or different, each designates hydrogen, alkyl or aryl, to a process for the production of these and to pharmaceutical preparations containing these novel compounds as active ingredient.

The compounds of the above formula I can be produced by a ring-closure reaction. Two routes of synthesis for the production of such compounds are:

a. First preparing 3-hydroxymethyl-3-quinuclidinol by reacting 3-carbomethoxy-3-quinuclidinol with a reducing agent, such as metallic hydrides (as for example lithium aluminum hydride) in a suitable reaction medium, such as a high ether (for example in tetrahydrofuran), under reflux; treating the reaction mixture with a lower alkyl acetate (such as methyl acetate or ethyl acetate) in an atmosphere of an inert gas, followed by treatment with an aqueous base (such as sodium hydroxide), followed by washing with water, to give the desired product;

b. Preparing quinuclidine 3-epoxide by reacting dimethylsulfoxonium methylide with quinuclidin-3-one;

The products of each of the above reaction steps (a) and (b) can be reacted with an aldehyde ($R_1$—CHO) or with a ketone ($R_1$—CO—$R_2$), wherein $R_1$ and $R_2$ are each alkyl or aryl, to result in the desired compounds of Formula I.

The novel compounds of Formula I are characterized by interesting and valuable pharmacological properties. They can be used as active ingredients of pharmaceutical preparations to be used in human and in veterinary medicine.

For example, the compound 2-methyl-spiro(1,3-dioxolane-4,3')quincolidine is a specific and powerful cholinergic stimulant and it has a high degree of specificity towards autonomic ganglionic and central muscarinic receptors located in the peripheral sympathetic ganglia or in the central nervous sytem. Due to its high degree of specificity for these sites, it can be used to activate these receptors under conditions when acetylcholine is lacking at the sites.

Amongst conditions in which this compound can be used there may be mentioned those requiring treatment with acetylcholine-like drugs, such as Huntingtons chorea, tardive dyskinesia or hyperkinesia and also in mental disturbances due to a deficiency of central acetylcholine resulting in mental disorder. Such deficiencies may be spontaneous or these may be drug-induced. The above compound is also of use for the treatment of disorders requiring the application of a long-lasting cholinergic agent of mild local activity. Such agent is needed in disorders such as glaucoma, as the compound is not destroyed by the enzyme which desactivates acetylcholine.

The compound 2-methyl spiro (1,3-dioxolane-4,3') quinuclidine or its cis-isomer may be used for the treatment of myestenia gravis.

The compound 2,2-diphenyl-spiro(1,3-dioxolane-4,3')-quinuclidine is a powerful anticholinergic agent and it may be used for the treatment of disorders due to an excess of acetylcholine, whether this be spontaneous or drug-induced. It is of use in the treatment of various diseases, such as Parkinson's diseases, of mental depression and it can also be used as adjunct in surgery instead of atropine, scopolamine etc. It may also be used in ophthalmology when prolonged mydriasis is required for diagnostic or for therapeutical purposes.

The compound 2,2-diphenyl spiro (1,3-dioxolane-4,3') quinuclidine and its salts may be used in ophthalmological preparations for inducing sustained mydriasis. This compound and its salts may also be used for the treatment of disorders characterized by an excess of central or peripheral acetylcholine-like activity, of intoxication by organophosphorous compounds or by carbamates, and for the treatment of conditions wherein central dopaminergic activity is pathologically reduced.

DESCRIPTION OF THE PREFERRED EMBODIMENT

The preparation of compounds according to the present invention is illustrated by way of example with reference to the following examples, which are to be construed in a non-limitative manner. Degrees are degrees centigrade.

EXAMPLE 1

Preparation of 2-Methyl spiro (1,3-dioxolane-4,3')Quinuclidine

To a stirred suspension of 17.5 g. lithium aluminum hydride in 100 ml dry tetrahydrofuran there was added during 1 hour a solution of 3-carbomethoxy-3-quinuclidinol tetrahydrofuran, 50 g in 100 ml. This was prepared according to Grob. Helv. Chim. Acta, 37, 1689 (1954). The reaction mixture was refluxed during 4½ hours, treated with 20 ml ethyl acetate under nitrogen, then with water (17 ml) then with 15% aqueous sodium hydroxide (17 ml.), and again with water, 51 ml. The resulting mixture was filtered and the filtrate was evaporated under reduced pressure, leaving as residue a syrup, 35 g., comprising 3-hydroxymethyl-3-quinuclidinol. A quantity of 5 g. of this syrup was treated with 20 ml. acetaldehyde and 20 ml. of methylene chloride. The resulting emulsion was cooled to 0° C and treated under agitation with 20 ml boron trifluoride ethereate for 1 hour. The resulting mixture was then poured on water containing an excess of potassium hydroxide and stirred until a complete decomposition of boron trifluoride had taken place. The mixture was extracted with ether and the extract was subjected to evaporation under reduced pressure. The residue consisted of crude 2-methyl spiro (1,3-dioxolane-4,3') quinuclidine, B.P.=68°-72° at 0.2 mm-Hg , $R_f$ on neutral alumina (ethyl acetate) = 0.6; M+ - 183. This product consists of a mixture of the two isomers wherein the methyl group is in one case in the cis-position (70%), the other in the trans-position (30%) respective to the nitrogen of the ring. The mixture was resolved into the two isomers by column chromatography on neutral alumina with ethyl acetate. The hydrochlorides of these were prepared by treatment of the two substances in dry acetone with gaseous hydrogen chloride, M.P. (cis-isomer) 233.8° (dec.); of the mixture : 234.2° (dec.).

EXAMPLE 2

2,2-dimethyl spiro (1,3-dioxolane-4,3') Quinuclidine

Dimethylsulfoxonium methylide was prepared by the method of Corey et al., Organic Synth. 49, 78 (1969) from 17.2 g. sodium hydride, 88 g. trimethylsulfoxonium iodide in 455 ml of dimethylsulfoxide in a 1 liter reaction flask equipped with a mechanical stirrer, reflux condenser and gas inlet tube, protected from moisture. After completion of the reaction, the gas inlet tube was replaced with a pressure compensated dropping funnel containing quinuclidine-3-one, 39 g. in dry dimethylsulfoxide, 129 ml. This was added to the dimethylsulfoxinium methylide during a period of 5 minutes, followed by stirring during a further 15 minutes at ambient temperature, followed by heating to 55°–60° during 2 hours on a water bath. The reaction mixture was poured into 200 ml. of cold water and extracted with five portions of 200 ml each of benzene. The extracts were combined, washed with water (100 ml), with 100 ml of saturated aqueous sodium chloride; dried over anhydrous magnesium sulfate and evaporated, yielding crude quinuclidine-3- epoxide, B.P.=55°–60° at 0.5 mm/Hg. The crop was 21 g., i.e. a yield of 49%. $R_f$ on neutral alumina (ethyl acetate) 0.3; $M^+$ = 139; hydrochloride salt: 200. 7–202°.

3.5 g of the epoxide were treated with 50 ml acetone and 30 ml boron trifluoride ethereate at 0°, with stirring. The stirring was continued during 48 hours at ambient temperature and after this decomposed by pouring into cold water containing an excess of potassium hydroxide. The organic phase was extracted with 100 ml ether, separated and dried over anhydrous magnesium sulfate. After evaporation of the solvent there was obtained a clear syrupy substance, 5g, 2,2-dimethyl spiro(1,3-dioxolane-4,3')quinuclidine, B.P.=60°–70° at 1 mm Hg, yield 4 g (80%); hydrochloride salt: M.P. = 245°–245.5°.

EXAMPLE 3

2,2-diphenyl spiro (1,3-dioxolane-4,3')quinuclidine

This compound was prepared via both the routes of Example 1 and of Example 2, using benzophenone. The M.P. = 105.5°–105.6°. The yield was 10–20 percent. Hydrochloride salt: M.P. = 204°–206°. $R_f$ TLC on alumina with chloroform: 0.4(free base).

Various other compounds within the ambit of Formula I were prepared by these routes, either via 3-hydroxymethyl-3-quinuclidinol or quinuclidine-3-epoxide by reaction with an aldehyde $R_1$—CHO or with a ketone $R_1$—CO—$R_2$, where $R_1$ and $R_2$ are as defined with respect to Formula I.

Compounds of Formula I, wherein $R_1$ differs from $R_2$, exist as two stereoisomers, namely a cis- and a trans-isomer. These can be resolved by conventional means, such as for example by column chromatography. The compound wherein $R_1$=methyl and $R_2$=H was resolved and it was found that the mixture consisted of about 30% by weight trans- and about 70% cis-siomer. The cis-isomer has a greater biological activity, and in the following Tables the activity of the substantially pure cis-isomer of this compound is given.

The compounds of the prepsent invention can be formulated into pharmaceutical compositions of matter by conventional means and by the use of conventional diluents, adjuvants and the like. They can be administered per os, by injection, by infusion etc. The dosage of the compound of Formula I, wherein $R_1$=methyl, $R_2$=H is about 0.2 mg to 3.0 mg/kg per day for adults, if given by injection; the oral dosage has to be about 2 to 3 times as large. The diphenyl compound, by parenteral administration is to be given in dosages of from about 1 to 5 mg per day for adults. The diphenyl compound can be effectively used in the form of ophthalmological preparations, together with suitable adjuvants, buffers or the like, and compositions of 0.5 to about 2% by weight give satisfactory results.

It is clear that the dosage and the route of administration have to be adjusted according to the disease or disorder to be treated and according to the severity of same.

The following tables indicate some of the uses of the novel compounds and of pharmaceutical preparations containing these, and these are compared with some conventional compounds used for similar applications.

It is clear that the description is by way of example only and that these merely serve to illustrate the invention.

TABLE 1

| | MUSCARINIC ACTIVITY OF VARIOUS COMPOUNDS | | | | | | | |
|---|---|---|---|---|---|---|---|---|
| | IN VIVO | | | | FALL | | | |
| | SCG STIMULATION | | INDUCED TREMORS | | BLOOD PRESSURE | | EPMR | IN VITRO |
| | | | | | | | | Guinea pig ileum induced contraction |
| COMPOUND | $ED_{50}$ ug | cat (ia) (umole) | $ED_{50}$ mg/kg | mice (ip) umole/kg | $ED_{50}$ µg/kg | cat (iv) nmole/kg | | $EC_{50}(M)$ | EPMR |
| Acetylcholine | 40 | 0.16 | not | applicable | 0.04 | 0.16 | 1 | $5 \cdot 10^{-8}$ | 1 |
| Acetyl-β-methyl choline | 50 | 0.22 | not | applicable | | | | $1.8 \cdot 10^{-7}$ | 3.6 |
| 3-Acetoxyquinuclidine | 50 | 0.24 | 7.5 | 36.5 | 0.2 | 1 | 6.25 | $7 \cdot 10^{-7}$ | 14 |
| I,$R_1$=H,$R_2$=—$CH_3$.HCl | 50 | 0.23 | 4.5 | 20.5 | 6.6 | 30.1 | 188 | $1.2 \cdot 10^{-5}$ | 240 |

*with 95% confidence limits (Litchfield et al, 1949)
**EPMR: equipotent molar ratio relative to ACh. nmole: nannomoles

TABLE 2

| | Acute Toxicity, tremorigenic and sialigenic Activity in Mice | | | | |
|---|---|---|---|---|---|
| | Acute Toxicity | Tremors | | Salivation | |
| COMPOUND | $LD_{50}^*$, mg/kg | $ED_{50}$(ip)* mg/kg | umole/kg | $ED_{50}^*$ (ip) mg/kg | umole/kg |
| 3-Acetoxy-quinuclidine | 112.5 (sc) | 7.5 | 36.5 | 1.8<br>2.9** | 8.8 |
| I,$R_1$=H;$R_2$=$CH_3$.HCl | 220 (sc) | 4.5 | 20.5 | 3.0 | 13.7 |

TABLE 2-continued

| | Acute Toxicity, tremorigenic and sialigenic Activity in Mice | | | | |
|---|---|---|---|---|---|
| | Acute Toxicity | Tremors | | Salivation | |
| COMPOUND | $LD_{50}$*, mg/kg | $ED_{50}(ip)$* mg/kg | umole/kg | $ED_{50}$* (ip) mg/kg | umole/kg |
| Oxotremorine | 5 (ip) | 0.14 | 0.73 | 0.12 | 0.63 |

*with 95% confidence limits, Litchfield & Wilcoxon, (1949).
**Chiang & Leaders, 1971

TABLE 3

| The Activity of Compound $I, R_1 = R_2 =$ phenyl, HCl and of Atropine Sulfate in various systems | | |
|---|---|---|
| | $I, R_1 = R_2 =$ phenyl, HCl | Atropine Sulphate++ |
| Guinea-pig ileum, log Ki | −9.6 | −9 |
| SCG (cat), antagonism to McN-A-343 induced contraction of NM $ED_{50}$, μmole (ia) | 0.5 | 1.4 |
| Mice | | |
| $LD_{50}$, mg/kg (sc) | 40(34.5–46.5) | >100 |
| Relative mydriatic activity | 1.5 | 1 |
| Antagonism to Oxotromorine induced salivation** $ED_{50}$* μmole/kg (sc) | 0.28(0.2–0.33)+ | 0.039(0.026–0.058)++ |
| Antagonism to Oxotromorine induced tremors*** $ED_{50}$* μmole/kg (sc) CNS/PNS activity*,# | 0.31(0.27–0.35)+ 1.1(0.77–1.56) | 1(0.75–1.40)++ 25.9(15.5–43.5) |
| Antagonism to Physostigmine## induced lethality $ED_{50}$*, μmole/kg (sc) | 0.20(0.19–0.23)+ | 8.05(6.7–8.9)++ |

*With 95% confidence limits (Litchfield and Wilcoxon, 1949).
**Oxotromorine, 170 μg/kg, ip (1.15 $ED_{50}$) induced salivation.
***Oxtromorine, 200 μg/kg, ip (1.15 $ED_{50}$) induced tremors.
Obtained by dividing $ED_{50}$ for blockade of tremors by $ED_{50}$ for blockade of salivation.
Physostigmine salicylate 3 mg/kg, ip (2 $LD_{50}$) induced lethality.
+$R_1 = R_2 = \Phi$,HCl is injected 20 min. prior to oxotromorine or physostigmine salicylate.
++Atropine Sulphate is injected 15 min. prior to oxotromorine or physostigmine salicylate.

We claim:

1. A compound selected from the group consisting of spiro (1,3-dioxolane-4,3') quinuclidines of the formula

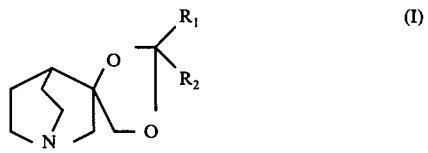

wherein $R_1$ and $R_2$ are each selected from the group consisting of hydrogen, lower alkyl, and phenyl, and physiologically compatible salts thereof.

2. A compound according to claim 1, wherein $R_1$ is hydrogen and $R_2$ is methyl; 2-methyl spiro (1,3-dioxolane-4,3') quinuclidine, in the form of in the form of the cis isomer or trans isomer or mixtures thereof.

3. A compound according to claim 1, wherein $R_1$ and $R_2$ are methyl: 2,2-dimenthyl spiro (1,3-dioxolane-4,3') quinuclidine.

4. A compound according to claim 1, wherein $R_1$ and $R_2$ are phenyl: 2,2-diphenyl spiro (1,3-dioxolane-4,3') quinuclidine.

5. A pharmaceutical composition for treatment to effect cholinergic stimulation, or for the treatment of manifestations of glaucoma, or for the treatment of myestenia gravis, which comprises a corresponding treatment effective amount of the compound of claim 2 and a suitable carrier.

6. The pharmaceutical composition of claim 5 for effecting cholinergic stimulation wherein the active ingredient is the cis-isomer of 2-methyl spiro (1,3-dioxolane-4,3') quinuclidine, or a salt thereof.

7. A pharmaceutical composition for treatment to induce sustained mydriasis, or for the treatment of disorders characterized by an excess of central or peripheral acetycholine-like activity, of intoxication by organo-phosphorus compounds or by carbamates, or for the treatment for conditions where central dopaminergic activity is pathologically reduced, which comprises a corresponding treatment effective amount of the compound of claim 4 or a salt thereof and a suitable carrier.

8. A process for treating disorders due to a deficiency of acetylcholine in the central nervous system which comprises administering an acetylcholine deficiency treating effective amount of the compound of claim 2.

* * * * *